United States Patent [19]

[11] 4,170,647

Gustafson et al.

[45] Oct. 9, 1979

[54] METHOD FOR THE CONTROL OF *ARIZONA HINSHAWII* IN POULTRY WITH AN ALKYLATED BM123γ-TYPE ANTIBIOTIC

[75] Inventors: Richard H. Gustafson, Lawrenceville; Gordon A. Kemp, Princeton, both of N.J.

[73] Assignee: American Cyanamid Company, Stamford, Conn.

[21] Appl. No.: 925,662

[22] Filed: Jul. 17, 1978

[51] Int. Cl.[2] .................. A61K 31/71; A61K 31/415; A61K 31/35

[52] U.S. Cl. .................................. 424/181; 424/272; 424/273 R; 424/283

[58] Field of Search ............... 424/181, 272, 273, 283

[56] References Cited

U.S. PATENT DOCUMENTS

| | | | |
|---|---|---|---|
| 4,007,167 | 2/1977 | Martin et al. | 424/181 |
| 4,018,972 | 4/1977 | Hlavka | 424/181 |
| 4,048,431 | 9/1977 | Hlavka et al. | 424/181 |

*Primary Examiner*—Sam Rosen

*Attorney, Agent, or Firm*—H. G. Jackson

[57] ABSTRACT

The invention relates to a method for the control of *Arizona hinshawii* in poultry, and especially in young turkey poults, comprising administering to the birds parenterally an effective amount of an alkylated BM123γ-type antibiotic, preferably isopropyl BM123γ. The invention further relates to a method for the control of transmission of *A. hinshawii* via the eggs of the birds, comprising contacting the eggs of the birds with solutions of the antibiotics. The invention also relates to alkylated BM123γ-type antibiotics, and especially to isopropyl BM123γ useful for the control of *Arizona hinshawii*.

7 Claims, No Drawings

METHOD FOR THE CONTROL OF *ARIZONA HINSHAWII* IN POULTRY WITH AN ALKYLATED BM123γ-TYPE ANTIBIOTIC

Arizonosis is an avian disease encountered worldwide, and is one of the most serious diseases of turkeys. The pathogen, *Arizona hinshawii,* is a motile bacteria which conforms to the definition of the family, Enterobacteriaceae, and is closely related to members of the genus, Salmonella, and also resembles some Citrobacter (*Escherichia freundii*) strains.

Transmission of the above disease may occur through infected hatching eggs, by contaminated feed and water, by contact between diseased and healthy birds, and by the placement of healthy birds into an environment contaminated with the pathogen. Although all ages of turkeys may be infected, adult birds usually are without symptoms, while young poults day-old 21 days of age are the most vulnerable, with a high rate of mortality. Thus, Arizonosis represents a problem of considerable economic importance to the turkey industry. Additionally, but equally important is the fact that Arizonosis may be transmitted to human beings, causing Salmonella-like infections. Control of this disease is, therefore, highly desirable.

We now find that by the novel method of the invention, *Arizona hinshawii* infections in poultry, and particularly in turkeys, can be controlled by administering to the birds parenterally or orally an effective amount of antibiotic BM123 γ of the structure represented by formula (I):

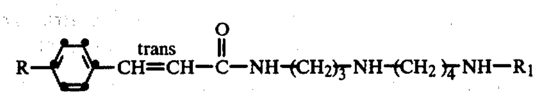

wherein $R_1$ is hydrogen, alkyl $C_1$–$C_{10}$, or alkyl $C_2$–$C_6$ monosubstituted with halo or hydroxy; and wherein R is a moiety of:

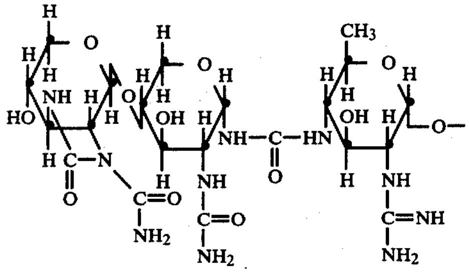

or

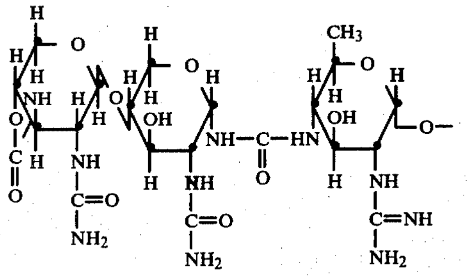

and mixtures thereof; and pharmaceutically acceptable salts thereof.

A preferred group of compounds represented by formula (I) are those, wherein $R_1$ is hydrogen, isopropyl, 1,3-dimethylbutyl, 1,3,3-trimethylbutyl, 1,2-dimethylpentyl, 1-methylnonyl, 1-ethyl-3-chloropropyl or 1-methyl-2-hydroxypropyl.

The most preferred antibiotic of formula (I) is the compound wherein $R_1$ is isopropyl. Hereinafter, this compound is also referred to as isopropyl BM123γ.

Pharmaceutically acceptable acids, which may be used to prepare salts of the above antibiotics, are, among others, hydrochloric acid, sulfuric acid, phosphoric acid, citric acid, tartaric acid, and the like.

The preparation and properties of the above BM123γ antibiotics are set forth in U.S. Pat. Nos. 4,007,167 (issued Feb. 8, 1977), No. 4,018,972 (issued Apr. 19, 1977) and No. 4,043,431 (issuedSept. 13, 1977). The above cited U.S. patents are hereby incorporated by way of reference.

In accordance with this invention, *Arizona hinshawii* can be effectively controlled by administering a hereinabove-identified antibiotic of formula (I), and preferably isopropyl BM123γ to poultry, and more particularly to turkeys in an amount from about 0.05 mg to 1.0 mg per bird, and preferably 0.12 mg to 0.5 mg per bird, in the form of one or more subcutaneous or intramuscular injection(s) as required to maintain an effective concentration in the birds' circulatory system until control of the pathogen is achieved.

In practice, the active material is formulated as injectables using pharmaceutically acceptable solvents, buffers, preservatives, and other additives.

Injectables for subcutaneous or intramuscular adinistration may be prepared by dissolving an antibiotic of formula (I), and preferably isopropyl BM123γ, or a pharmaceutically acceptable salt thereof at a concentration of from 1% to 20% w/v, and preferably 1% to 5% w/v in distilled water, wherein the solution may also contain 0.6% to 0.8% w/v of a phosphate or citrate buffer, and the like; 0.4% to 0.6% w/v of sodium chloride, preservatives such as methyl paraben, propyl paraben, and the like, in amounts of from 0.1% to 0.2% w/v, a chelating agent such as disodium edetate, and the like. If desired, some of the water may be replaced in the formulations with water-miscible and pharmaceutically acceptable solvents such as propylene glycol, glycerol, glycerol formal, and the like.

Alternatively, a premeasured amount of freeze-dried antibiotic of formula (I) may be prepackaged in multiple unit dosages in sterile vials, and reconstituted with predetermined volumes of sterile water, isotonic saline solution, mixtures of water - propylene glycol, -glycerol - glycerol formal, and the like, prior to use.

The invention also relates to a method for the control of transmission and dispersal of *A. hinshawii* via the eggs of poultry, and especially turkeys, comprising dipping the eggs of the birds in solutions of antibiotics of formula (I), and especially isopropyl BM123γ. Should it be desired, the eggs may be sprayed, or treated by other suitable methods, with solutions of antibiotics.

The following non-limiting examples serve to further illustrate the novel method of the invention.

EXAMPLE 1

Evaluation of the Efficacy of Antibiotic Isopropyl BM123γ for the Control of *Arizona hinshawii* in Turkey Poults.

Test Drug.

Antibiotic Isopropyl BM123γ (hydrochloride) dissolved in sterile, double distilled water for subcutaneous injection. Dosage levels per bird are given in Table I.

Test Animals.

Female, broad-breasted, bronze turkey poults, Lovelace strain, one day old on day of challange.

At each dose level, and for controls, two replicates (A and B) are used, and there are ten poults per replicate (a total of 200 birds) each. The poults are distributed into equal weight groups (two replicates per group) and caged without feed. One group of poults serves as noninfected, nonmedicated controls, and one group serves as infected, unmedicated controls.

Pathogen.

*Arizona hinshawii* 9503, serotype 7:1,7,8 [nalidixic acid resistant ($NA^r$)].

The bacterial culture is prepared by inoculating a loopful of *A. hinshawii* 9503 into 9 ml trypticase soy broth, and the culture incubated for 18 hours at 37° C. on a shaker. The culture is then adjusted to 44% transmission at 645 mμ to yield approximately $10^8$ colony forming units (CFU) per ml.

Procedure

The bacterial culture is serially diluted for plate counts and 0.5 ml of the $10^4$ culture, in 0.85% sterile saline is injected intraperitoneally into each bird, with the exception of those serving as noninfected controls. In the same handling, each bird in the treated groups is medicated with the appropriate drug by injection of a sufficient volume of a 0.2 mg/ml solution of same, to correspond to the dosages given in Table I, given subcutaneously at the base of the neck. The duration of the trial is 12 days during which the poults are offered Turkey Diet No. 527 (table of composition appended hereto) and water *ad libitum*.

All birds are examined daily, post-challange, for mortality, and the amount of infecting A. hinshawii recovered from the livers of dead birds is also determined.

The data thus obtained are summarized in Table I below.

| TURKEY DIET NO. 527 | |
|---|---|
| Ground Yellow Corn | 40.90% |
| Soybean Oil Meal (50%) | 43.30 |
| Menhaden Fish Meal | 7.50 |
| Stabilized Fat | 3.00 |
| Dicalcium Phosphate | 2.00 |
| Ground Limestone | 1.30 |
| Brewers Dried Yeast | 1.25 |
| Iodized salt | 0.25 |
| *Premix | 0.50 |
| | 100.00 |

*Premix for One Ton:

-continued

| TURKEY DIET NO. 527 | |
|---|---|
| $MnSO_4$ | 150.0 grams |
| Vitamin A (30,000 μ/g) | 333.3 |
| Vitamin $D_3$ (200,000 μ/g) | 10.0 |
| Choline Chloride (50%) | 1135.0 |
| Merck Vitamin Mix #1231 | 284.0 |
| Niacinamide | 45.4 |
| Tocopherol Succinate (Vitamin E) | 5.0 |
| Vitamin K (Menadione) | 1.0 |
| Parvo (10%) Folic Acid | 8.2 |
| Proferm (20 mg/lb) $B_{12}$ | 227.0 |
| Fine Ground Corn | 2337.1 |
| | 4536.0 |

Table I

Evaluation of the Efficacy of Antibiotic Isopropyl BM123γ for the Control of *Arizona hinshawii* in Turkey Poults, as Compared to Gentamicin

| Treatment | Dosage: mg/Bird | *A. hinshawii* Challange | Survivors Replicates A | Survivors Replicates B | Survivors Total | Dead Birds | Recoverable *A. hinshawii* ($NA^r$)* from the Livers of Dead Birds: Number of Dead Birds | Recoverable *A. hinshawii* ($NA^r$)* from the Livers of Dead Birds: $\log_{10} \bar{X}$ CFU/g** |
|---|---|---|---|---|---|---|---|---|
| Control | — | No | 10 | 9 | 19 | 1 | — | — |
| Control | — | Yes | 4 | 3 | 7 | 13 | 13 | 6.14 |
| Antibiotic | 0.25 | Yes | 10 | 10 | 20 | 0 | 0 | — |
| Isopropyl BM123γ | 0.12 | Yes | 9 | 8 | 17 | 3 | 2 | 4.09 |
| | 0.06 | Yes | 4 | 8 | 12 | 8 | 5 | 4.17 |

*($NA^r$) - Nalidixic acid resistant.
**CFU/g - Colony forming units/g.

EXAMPLE 2

In vitro Activity of BM123γ HCl Against Six Strains of *Arizona hinshawii*, Using Gentamicin as Standard.

Serial, two-fold dilutions of drugs are prepared in trypticase soy broth (TSB). To each tube containing 5 ml of broth is added 0.1 ml of a $10^{-3}$ dilution of bacterial inoculum (six strains of *Arizona hinshawii*, originally isolated from clinical cases of Arizonosis of turkeys), adjusted prior to dilution to 44% transmission at 645 mμ. An inoculated broth, containing no drug is included as growth control for each strain tested. The minimum inhibitory conentration (MIC) is read as the highest dilution of drug showing no visble growth after 24 hours incubation at 37° C. The results obtained are shown in Table II below.

TABLE II

In vitro Efficacy of BM123γ HCl for Inhibiting the Growth of *Arizona hinshawii* strains, Using Gentamicin as Standard

| Pathogen | Isolate Number | Minimum Inhibitory Concentration (mcg/ml): BM123γ HCl | Minimum Inhibitory Concentration (mcg/ml): Gentamicin |
|---|---|---|---|
| *Arizona hinshawii* | 1 | 0.12 | 2 |
| | 2 | 0.12 | 2 |
| | 3 | 0.12 | 2 |
| | 4 | 0.12 | 2 |
| | 5 | <0.06 | 2 |
| | 6 | 0.12 | 2 |

EXAMPLE 3 In vitro Antibacterial Activity of Antibiotic Isopropyl BM123γ.

Pathogens are obtained fo diseased turkey poults. Minimal inhibitory concentration (MIC) is determined for *Arizona hinshawii* by the method of Example 2. The results obtained are given in Table III below.

TABLE III

Minimal Inhibitory Concentration (MIC) of Antibiotic Isopropyl BM123γ Against *Arizona hinshawii*

| | | Number | MIC (mcg/ml) | |
|---|---|---|---|---|
| Pathogen | Source | of Isolates | Range | Median |
| *Arizona hinshawii* | Turkeys | 7 | 0.125–0.25 | 0.125 |

We claim:

1. A method for the control of *Arizona hinshawii* infections in poultry comprising, administering parenterally or orally to the birds an effective amount for the control of the infections of antibiotic BM123γ of formula:

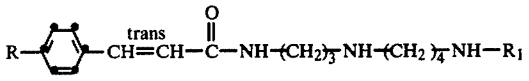

wherein $R_1$ is selected from hydrogen, alkyl $C_{1}$-$C_{10}$, or alkyl $C_{2}$-$C_{6}$ monosubstituted with halo or hydroxy; R represents a moiety:

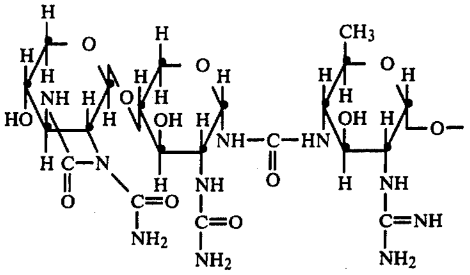

or

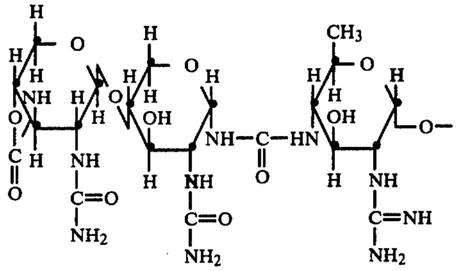

and mixtures thereof; and pharmaceutically acceptable salts thereof.

2. A method according to claim 1, wherein $R_1$ is hydrogen, isopropyl, 1,3-dimethylbutyl, 1,3,3-trimethylbutyl, 1,2-dimethylpentyl, 1-methylnonyl, 1-ethyl-3-chloropropyl and 1-methyl-2-hydroxypropyl; pharmaceutically acceptable salts thereof.

3. A method according to claim 1, wherein $R_1$ is isopropyl.

4. A method according to claim 1, wherein the pharmaceutically acceptable salts are hydrochloride, sulfate, phosphate, citrate or tartrate.

5. A method according to claim 1, wherein the antibiotic is administered in amounts of from 0.05 mg to 1.0 mg per bird.

6. A method according to claim 1, wherein the birds are turkeys.

7. A method according to claim 1, wherein antibiotic isopropyl BM123γ is administered parenterally to turkey poults in amounts from 0.06 mg to 0.5 mg per bird.

* * * * *